United States Patent
Alshehri et al.

(10) Patent No.: US 12,245,787 B2
(45) Date of Patent: Mar. 11, 2025

(54) TISSUE FORCEPS WITH WIDE JAW

(71) Applicant: KING SAUD UNIVERSITY, Riyadh (SA)

(72) Inventors: Mohamed Abduallah Alshehri, Riyadh (SA); Abdullah Awadh Alamri, Riyadh (SA); Sami Hussain Alqahtani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/225,996

(22) Filed: Jul. 25, 2023

(65) Prior Publication Data

US 2025/0032144 A1    Jan. 30, 2025

(51) Int. Cl.
| | | |
|---|---|---|
| *A61B 17/30* | (2006.01) | |
| *A61B 17/00* | (2006.01) | |
| *A61B 17/28* | (2006.01) | |

(52) U.S. Cl.
CPC ............. *A61B 17/30* (2013.01); *A61B 17/00* (2013.01); *A61B 17/28* (2013.01)

(58) Field of Classification Search
CPC ..... A61B 17/0483; A61B 17/08; A61B 17/12; A61B 17/28; A61B 17/2812;
(Continued)

(56) References Cited

U.S. PATENT DOCUMENTS 5,019,092 A * 5/1991 Klintmalm ........... A61B 17/122
                                                                81/418
5,797,919 A * 8/1998 Brinson ............. A61B 17/8866
                                                                606/205
(Continued)

FOREIGN PATENT DOCUMENTS

| | | | |
|---|---|---|---|
| DE | 202006007496 U1 | 10/2006 | |
| GB | 2 073 086 | * 10/1981 | ............. A61B 17/28 |
| WO | WO-2017100608 A1 * | 6/2017 | ........... A61F 13/124 |

OTHER PUBLICATIONS

"Walter lid grasping forceps" sold by Anthony Products, Inc at https://www.anthonyproducts.com/store/walter-lid-grasping-forceps, accessed on May 8, 2023.
(Continued)

*Primary Examiner* — Sarah W Aleman
(74) *Attorney, Agent, or Firm* — Nath, Goldberg & Meyer; Joshua B. Goldberg (57) ABSTRACT

A method and device for grasping tissue using the tissue forceps with wide jaws. The tissue forceps include a first arm and a second arm joined at a vertex at a proximal end. The first arm and the second arm have distal portions which are extensions angled leftward away from the longitudinal axis of the first and second arms. Wide forceps jaws terminate the distal end of the angled extensions and the terminal inner surfaces of the jaws have serrated edges. The forceps is adapted to sequentially grasp tissue on opposed sides of a tissue interface and then present the tissue for further procedure. The jaws can be straight, convex, or concave to hold, stabilize and manipulate tissue flap borders with better grasping and control. The jaws can be in line with the handle (straight) or 45 or 90 degrees offset for better access to different surgical site's locations.

5 Claims, 5 Drawing Sheets

(58) Field of Classification Search
CPC .............. A61B 17/282; A61B 17/2833; A61B 17/2841; A61B 17/29; A61B 17/30; A61B 17/3201; A61C 3/14; B25B 7/02
See application file for complete search history.

(56) References Cited

U.S. PATENT DOCUMENTS

| | | | |
|---|---|---|---|
| 8,608,774 B1* | 12/2013 | Alshemari | A61B 17/30 606/210 |
| 10,213,200 B2 | 2/2019 | Kim et al. | |
| 2006/0190033 A1* | 8/2006 | Molloy | A61B 17/282 606/205 |
| 2007/0049973 A1* | 3/2007 | Burbank | A61B 17/42 607/2 |
| 2008/0300622 A1* | 12/2008 | Xu | A61B 17/282 606/207 |
| 2017/0087009 A1* | 3/2017 | Badawi | A61F 7/02 |
| 2020/0345405 A1* | 11/2020 | Fishman | A61F 9/007 |

OTHER PUBLICATIONS

"Mueller putterman clamp" sold by Hayden Medical Inc. at https://www.haydenmedical.com/product/mueller-putterman-clamp/, accessed on May 8, 2023.

"Green fixation forceps" sold by Hayden Medical Inc. at https://www.haydenmedical.com/product/green-fixation-forceps/, accessed on May 8, 2023.

* cited by examiner

*FIG. 11*

TISSUE FORCEPS WITH WIDE JAW

BACKGROUND

1. Field

The present subject matter relates to surgical instruments, such as tissue forceps having a distal assembly for performing internal surgical procedures such as cutting, grasping, removing internal tissue, and/or compressing newly dissected tissue for bleeding control. More particularly, the present subject matter relates to tissue forceps with a wide jaw that enable holding, manipulating and stabilizing a bulk of tissue during surgical procedures for a variety of tissue samples.

2. Description of the Related Art

Surgical procedures involving the cutting, grasping, bleeding control, and/or removal of internal tissue for further analysis are frequently performed using various forms of surgical forceps. Surgery typically involves the dissection of one or more layers of tissue in order to gain access to damaged or diseased tissue for repair or removal. Sharp dissection (which involves cutting tissues) is usually performed using a surgical scalpel and/or surgical scissors. There are a variety of scalpels and scissors available for use in surgery. Each different scalpel and scissors are adapted to perform a particular sharp dissection function. Sharp dissection is usually followed by profuse bleeding from dissected tissues. Bleeding during surgery must be controlled to prevent blood from occluding tissues in the surgical operating field.

During such surgical procedures, forceps are used by the surgeon to grasp and occlude blood vessels in order to control bleeding while performing a puncture, ligation, suture, or cut. Traditionally, this grasping or gripping has been accomplished using numerous types of available tissue forceps. However, these instruments grip the intended tissue at a single point, and the above procedures are then performed in the proximity of the gripped site. Multiple forceps can be used to clamp blood vessels during a singular procedure based on the fact that the majority jaws in design are narrow and taper to a fine point.

Therefore, whether one or multiple forceps are used, the gripped point unilaterally acts as a pivot for the force of the needle, thread, scissors, or scalpel. As a result, the tissue turns on the gripped point, and a desired right angle cut or needle insertion is not possible.

Many designs have been proposed and manufactured in an attempt to avoid such difficulties. For example, non-toothed forceps have been used for fine handling of tissue and traction during dissection. Similarly, Adson Forceps, which are toothed at the tip, have been used for handling dense tissue. Bonney Forceps is a heavy forceps used for holding thick tissue. DeBakey Forceps have been used for atraumatic tissue grasping during dissection, and Russian Forceps have been used for atraumatic tissue grasping during dissection.

However, as the field of surgery advances, there is a greater need for instruments that can perform as accurately as possible. There are a few existing fork-like forceps that can grip tissue at two points and are theoretically capable of providing two pivots to perform the above-mentioned techniques.

However, these fork-like forceps, due to their structural design, are incapable of placing very close, millimeter-sized sutures, which is necessary during intestinal anastomoses. While many surgeons consider 3 to 5 mm acceptable for their intestinal anastomosis inter-suture distance, Juliet C et al., in their "Systematic review of the technique of colorectal anastomosis" in February 2013, explained that these surgeons are probably relying on their education and instinct more than on scientific evidence. In the only available study, Waninger J, Kauffmann G W, Shah I A, and Farthmann E H examined the "Influence of the distance between interrupted sutures and the tension of sutures on the healing of experimental colonic anastomoses" published in Am J Surg. 1992 March; 163(3):319-23. The results of this study demonstrated that the best healing pattern during anastomosis would be achieved by moderate sutures tension and a 1.5-mm distance between sutures.

All the above-described forceps have a narrow and pointed tip which makes it difficult to hold long and bulky tissue flaps, especially in a quadrant of full arch periodontal and implant dentistry surgical flaps. There are multiple solutions that have been presented in the prior art. However, these solutions are limited and restricted to their conventional architecture, and have considerable shortcomings which adversely affect the convenience with which they can be used. The prior systems have certain limitations including the design of assemblies which make them not suitable for every type of user. Moreover, the ease-of-use ability of these assemblies is also questionable.

What is needed is a tissue grasping forceps with wide jaws that allow for larger area of tissue to be clamped off such that the use of multiple forceps in a surgical operation is minimized as much as possible.

SUMMARY

The present subject matter is directed towards a method and device for using tissue grasping forceps for applying pressure to freshly dissected tissues during a surgical procedure. The present subject matter provides an assembly with a new approach of a tissue forceps, providing wide serrated jaws which are either straight, convex, or concave to enable the operator to hold, stabilize and manipulate tissue flap borders with better grasping and control. Furthermore, the jaws will be in line with the handle or at a 45 degree or a 90 degree offset for better access to different surgical site's locations.

The primary desirable object of the present subject matter is to provide a novel and improved form of a tissue forceps with a wide jaw that enable holding, manipulating and stabilizing a bulk of tissue during surgical procedures. Another object is to provide a method which assist doctors in providing a lightweight handheld tissue forceps that has wide serrated jaws which are straight, convex, or concave, thus enabling the operator to hold, stabilize and manipulate tissue flap borders with better grasping and control. This surgical tissue forceps can give the surgeon more control over their performance, thereby increasing control over a surgical site and enhancing both the speed and quality of the entire procedure.

The present forceps can have a unitary construction which is compatible with high volume manufacturing methods for all of the components. The low manufacturing cost means that this high-quality portable instrument may be made available to hospitals and clinics that may otherwise not be able to afford a quality instrument. It also makes the assembly highly applicable to the developing world and exposes a wider public audience to firsthand scientific advancements.

In a first aspect of the present subject matter, a device for grasping newly dissected tissue and applying pressure to said grasped tissue to prevent bleeding is provided, the device comprising: a first arm; a second arm, wherein the first arm and the second form a vertex at a first proximal end of the first and second arms. The first and the second arms are dimensioned to be straight for 12 cm before angling away at an angle of 30 degrees to the longitudinal axis of each arm. This angled extension of the arm for each arm is 2 cm in length. The distal end of each angled extension of the first and second arm, respectively, terminate in slightly arcuate jaws that at their midpoints are joined to the angled extension of the first and second arm, respectively. Each slightly arcuate jaw is also 2 cm in length and at each terminal portion each jaw on an inner surface is disposed a serrated portion or surface area for grasping purposes.

In an embodiment, the present device is a tissue forceps with wide jaws for compressing newly dissected tissue, comprising: a first arm traversing a first arm length, said first arm having a textured area on an outer surface of said first arm; a second arm traversing a second arm length where said second arm length is equal to said first arm length, wherein the first arm and the second arm form a vertex at a first proximal end of the first arm and second arm; a first extension extending from a distal end of said first arm away at a first extension angle with respect to a longitudinal axis of said first arm, wherein a distal end of said first extension terminates in a first forceps jaw; and a second extension extending from a distal end of said second arm away at a second extension angle with respect to a longitudinal axis of said second arm, wherein a distal end of said second extension terminates in a second forceps jaw, wherein said first forceps jaw has a first jaw length and said second forceps jaw has a second jaw length, wherein an inner surface of said first forceps jaw has a plurality of serrated surface areas and wherein an inner surface of said second forceps jaw has a plurality of serrated surface areas.

A second aspect of the present subject matter is a method which, when implemented with the device, performs the function of applying pressure to newly dissected tissue and thereby prevents bleeding. In this regard, the present subject matter relates to a method of compressing newly dissected tissue using tissue forceps with wide jaws, the method comprising: positioning the tissue forceps proximal to the newly dissected tissue such that a first arcuate forceps jaw and a second arcuate forceps jaw of the tissue forceps are adjacent the newly dissected tissue; squeezing a first arm of the tissue forceps connected to the first arcuate forceps jaw by applying pressure to a textured area along an outer surface of said first arm; squeezing a second arm of the tissue forceps connected to the second arcuate forceps jaw by applying pressure to a corresponding outer surface of a second arm of the tissue forceps such that the first arcuate forceps jaw and the second arcuate forceps jaw of the first arm and the second arm, respectively, clamp down and engage each other; and sandwiching the newly dissected tissue at non-textured areas of closing inner surfaces of the first arcuate forceps jaw and the second arcuate forceps jaw, respectively, such that a plurality of serrated areas on said first arcuate forceps jaw and said second arcuate forceps jaw engage each other.

These and other features of the present subject matter will become readily apparent upon further review of the following specification in conjunction with the accompanying drawings.

BRIEF DESCRIPTION OF THE DRAWINGS

Similar reference characters denote corresponding features consistently throughout the attached drawings.

DETAILED DESCRIPTION OF EMBODIMENTS

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All of the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

The terminology used herein is for the purpose of describing particular embodiments only and is not intended to be limiting.

As used herein, the term "and/or" includes any and all combinations of one or more of the associated listed items.

As used herein, the singular forms "a," "an," and "the" are intended to include the plural forms as well as the singular forms, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

In one embodiment, the present subject matter pertains to a sequential surgical forceps adapted to sequentially grasp tissue on opposed sides of a tissue interface. Once grasped in a sequential manner, the tissue can then be presented for capture and closure by a surgical fastening apparatus. The complete procedure of approximation and closure of a tissue wound can be accomplished by a single operator. The sequential tissue forceps can comprise a first arm, a second arm and a central arm wherein both the first arm and the second arm are sequentially closed with respect to the central arm. The first arm, second arm and central arm can comprise tips having an improved gripping surface to facilitate tissue capture and retention. In some embodiments, the central arm can comprise a pair of tips wherein a gap is presented between the tips that defines a mating interface to allow for selective positioning of the sequential tissue forceps and any captured tissue with respect to a surgical fastening apparatus. In this way, the present forceps can consistently manipulate and present wound tissue to the surgical fastening apparatus.

In another embodiment, the sequential tissue forceps does not include a defined mating interface on the center arm but still provides for bilateral tissue capture and retention in a sequential manner using the sequential tissue forceps.

In another aspect, the present tissue forceps has a wide serrated jaw which is straight, convex, or concave to enable the operator to hold, stabilize, and manipulate tissue flap borders with better grasping and control. At the same time, the jaws can be in line with the handle or offset by 45 degrees or 90 degrees for better access in the different surgical sites' locations. Through such a sequential closure of the first arm and second arm relative to the central arm, tissue on opposed sides of a wound can be sequentially grasped, retained and approximated under selective control of a user.

In an embodiment, the present device is a tissue forceps with wide jaws for compressing newly dissected tissue, comprising: a first arm traversing a first arm length, said first arm having a textured area on an outer surface of said first arm; a second arm traversing a second arm length where said second arm length is equal to said first arm length, wherein the first arm and the second arm form a vertex at a first proximal end of the first arm and second arm; a first extension extending from a distal end of said first arm away at a first extension angle with respect to a longitudinal axis of said first arm, wherein a distal end of said first extension terminates in a first forceps jaw; and a second extension extending from a distal end of said second arm away at a second extension angle with respect to a longitudinal axis of said second arm, wherein a distal end of said second extension terminates in a second forceps jaw, wherein said first forceps jaw has a first jaw length and said second forceps jaw has a second jaw length, wherein an inner surface of said first forceps jaw has a plurality of serrated surface areas and wherein an inner surface of said second forceps jaw has a plurality of serrated surface areas.

In an embodiment of the present tissue forceps, the first extension angle and the second extension angle are equal. In this regard, said first extension angle and said second extension angle can each be, by way of non-limiting example, about 30 degrees or about 90 degrees. Similarly, in a non-limiting embodiment, said first arm length and said second arm length are both about 12 cm. Likewise, in non-limiting embodiments, said first forceps jaw and said second forceps jaw can be 2 cm in length, arcuate in shape and/or can be in a bowed-out orientation.

In another embodiment, said first arm and said second arm are configured such that when they are squeezed together by applying pressure at said textured area on said outer surface of said first arm and applying pressure at a corresponding outer surface on said second arm, the first forceps jaw and the second forceps jaw close together compressing said newly dissected tissue and preventing bleeding from said newly dissected tissue.

Figure 1:
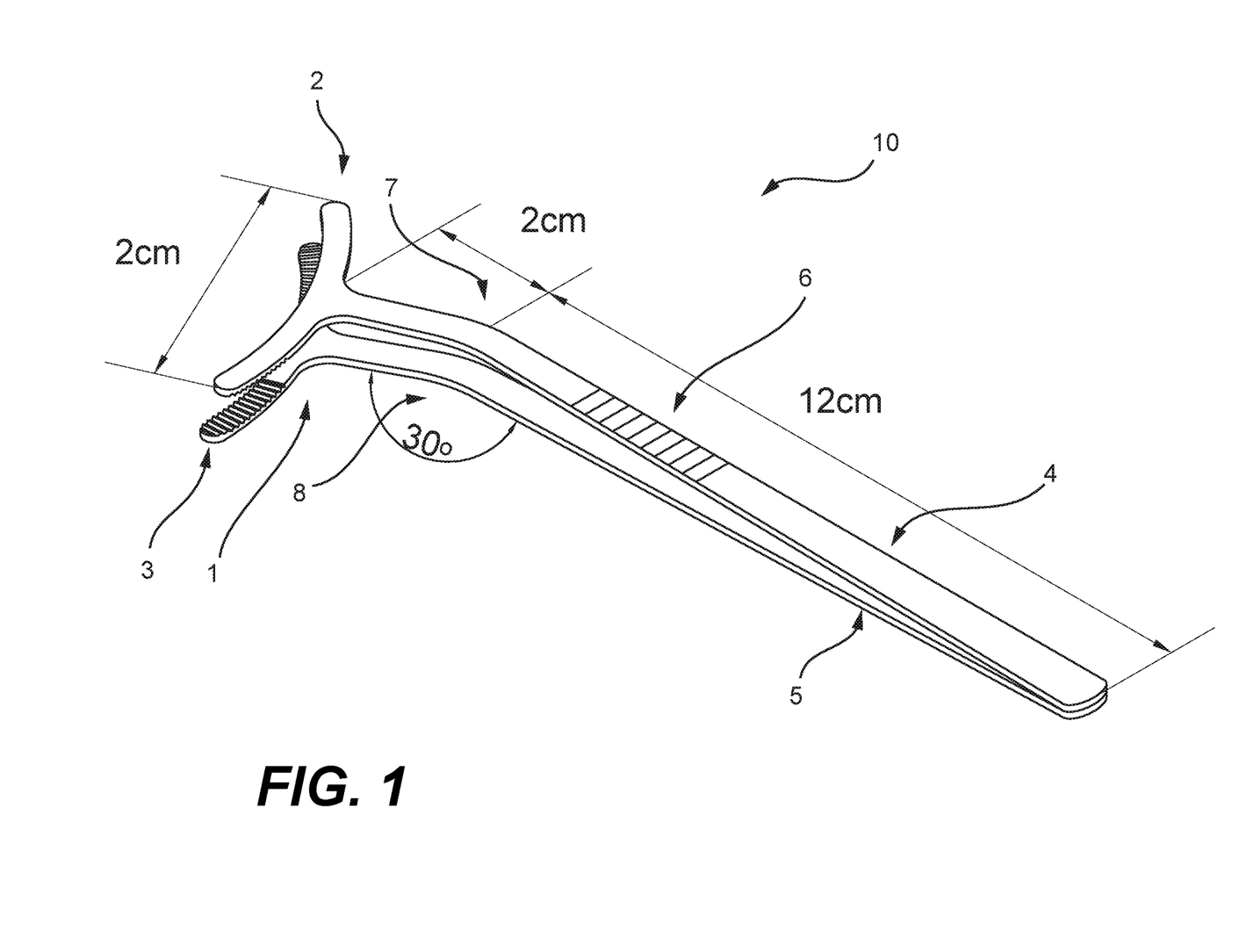
FIG. 1 is a ¾ view of the tissue grasping forceps with wide jaws including the dimensions of each portion of a specific embodiment of the device.

As shown in FIG. 1, a first embodiment of the tissue forceps with wide jaws is provided (10). The device comprises a first arm (4) that traverses a first portion and a second arm (5) that also traverses a first portion corresponding with the first portion of the first arm (4), wherein the first arm and the second form a vertex at respective first proximal ends of the first and second arms. In certain embodiments, one of both first portions can be about 12 cm in length, or about 10 cm to about 15 cm, about 10 cm, about 11 cm, about 12 cm, about 13 cm, about 14 cm, or about 15 cm in length.

The first and the second arms can be dimensioned to be straight or flat along the first portion before angling away from the longitudinal axis of each arm. In an embodiment, the first and second arms can be angled away at an angle of 30 degrees to the longitudinal axis of each arm. In an embodiment, this angled extension of the first arm (7) and the second arm (8) can each be about 2 cm in length, or about 1.5 cm to about 2.5 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, or about 2.5 cm in length.

At the distal end of each angled extension of the first arm (7) and second arm (8), the first and second arms respectively terminate into a slightly arcuate jaw that at its midpoint is perpendicular to the angled extensions of the respective first and second arms (7) and (8). Each jaw (1), (2) can also be 2 cm in length, in an embodiment, and at each terminal portion each jaw can have disposed on an inner surface a serrated portion or surface area (3) for grasping purposes. On the top surface of said first arm is a beveled or textured area (6) for grasping the instrument by one's hand such that the instrument won't slip or be dropped if the area were smooth. In certain embodiments, each jaw (1), (2), can be about 2 cm in length, or about 1.5 cm to about 2.5 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, or about 2.5 cm in length.

In operation, a squeezing pressure is applied at the beveled grip area (6) on the first arm and to a corresponding outer location on the second arm to draw the jaws together such that the newly dissected tissue is sandwiched between the closing surface along the non-serrated portions of the first jaw (2) and the second jaw (1), allowing the grooves of the serrated portion of the jaws (3) to interlock and firmly keep the dissected tissue tightly compressed and thus prevent any excess bleeding from occluding the surgical operational field. Once the need for the tissue forceps has passed, the jaws of the tissue forceps can be opened up and the instrument can be moved to the next area in the surgical field. Note the wide compression area due to the wide design of the jaws allows for larger areas of the dissected tissue to be addressed for treatment.

Figure 2:
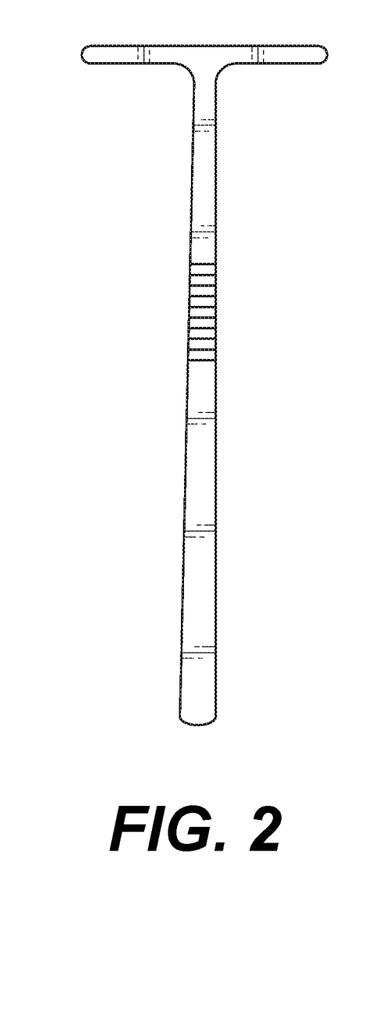
FIG. 2 is a top down view of the tissue grasping forceps with wide jaws where there is no angled extension of the arm and where the first and second jaws are perpendicular segments that attach to the distal portion of the arms at the midpoints of the first and second jaws.
Figure 3:
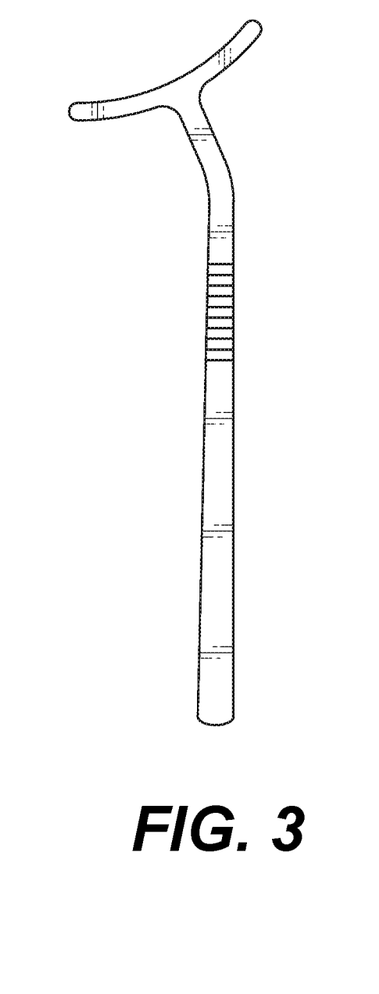
FIG. 3 is a top view of the tissue grasping forceps with arcuate wide jaws attached first and second 30 degree angled extensions of the first and second arms.
Figure 4:
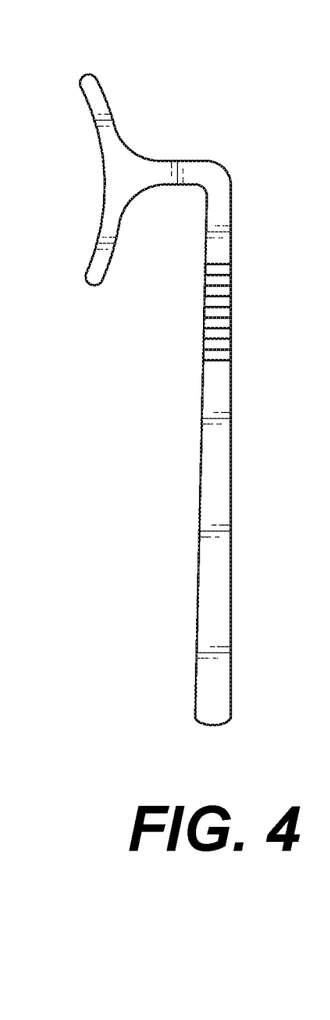
FIG. 4 is a top view of the tissue grasping forceps with arcuate wide jaws attached first and second 90 degree angled extensions of the first and second arms.

Other embodiments for the jaw design are contemplated. For instance, in FIG. 2, the tissue forceps with a wide jaw design includes a non-arcuate terminal jaw of 2 cm that is perpendicular to the first and second arms of the tissue forceps. In this embodiment, there is no angled extension of the first and second arms at a 30 degree orientation to the longitudinal axis of the first and second arms. FIG. 3 relates to the embodiment of FIG. 1. FIG. 4 is an embodiment of the tissue forceps with wide jaws of 2 cm where the angled extension of the first and second arms of the tissue forceps are at a right angle of 90 degrees.

Figure 5:
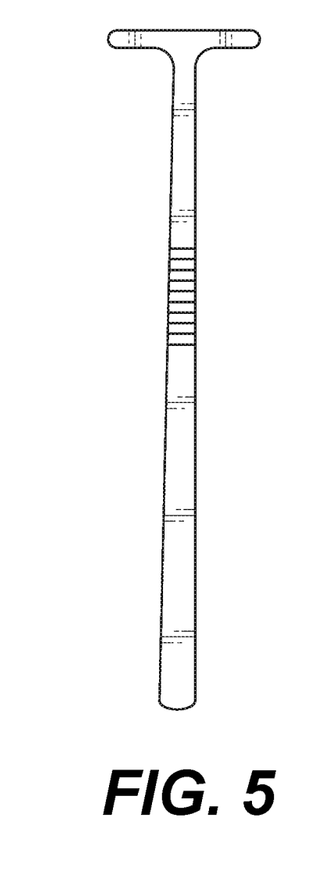
FIG. 5 is a top down view of the tissue grasping forceps with wide jaws where there is no angled extension of the arm and where the first and second jaws are perpendicular segments smaller in dimension than those of FIG. 2 such that the distal portion of the arms are attached at their midpoints.
Figure 6:
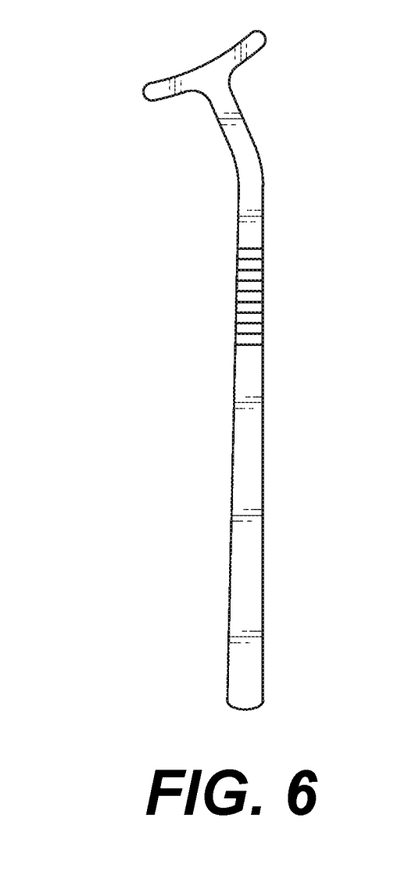
FIG. 6 is a top view of the tissue grasping forceps with arcuate wide jaws smaller in size than the arcuate jaws of FIG. 3 attached first and second 30 degree angled extensions of the first and second arms.
Figure 7:
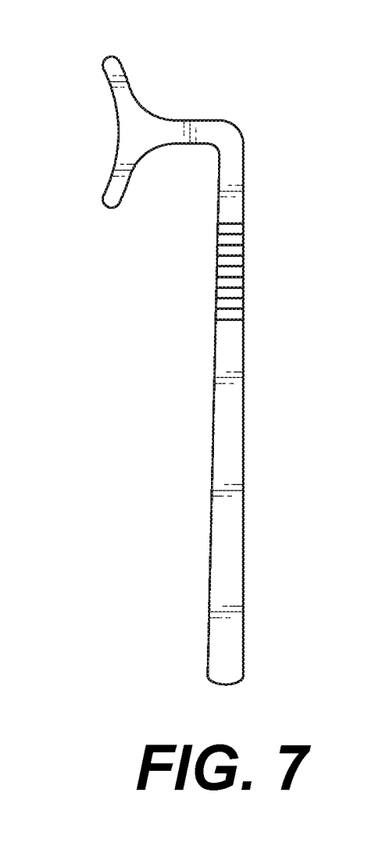
FIG. 7 is a top view of the tissue grasping forceps with arcuate wide jaws smaller in size than the arcuate jaws of FIG. 4 attached first and second 90 degree angled extensions of the first and second arms.

In FIG. 5, the tissue forceps with a wide jaw design includes a non-arcuate terminal jaw smaller than 2 cm that is perpendicular to the first and second arms of the tissue forceps. In this embodiment, there is no angled extension of the first and second arms at a 30 degree inclination. FIG. 6 relates to the embodiment of FIG. 3 but with the arcuate jaws also being smaller than 2 cm. FIG. 7 is an embodiment of FIG. 4 having the tissue forceps with wide jaws smaller than 2 cm in dimension where the angled extension of the first and second arms of the tissue forceps are at a right angle of 90 degrees.

Figure 8:
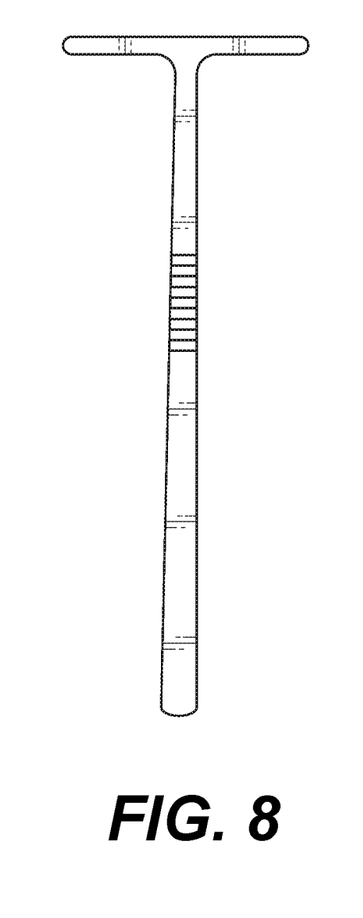
FIG. 8 is a top down view of the view of the tissue grasping forceps with wide jaws where there is no angled extension of the arm and where the first and second jaws are perpendicular segments that attach to the distal portion of the arms at their midpoints.
Figure 9:
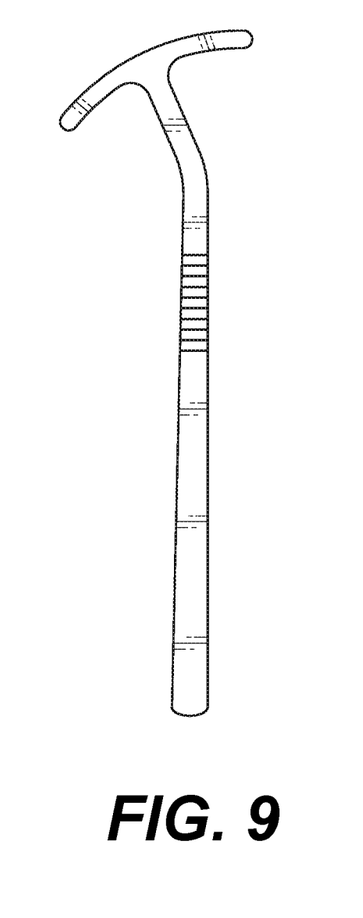
FIG. 9 is a top view of the tissue grasping forceps with bowed out arcuate wide jaws attached first and second 30 degree angled extensions of the first and second arms.
Figure 10:
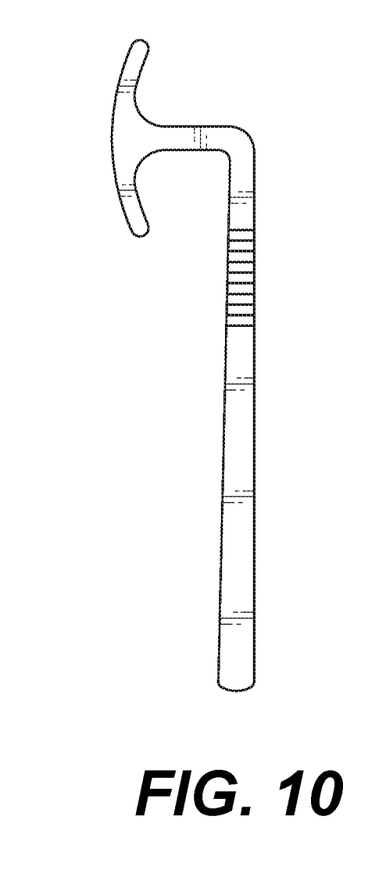
FIG. 10 is a top view of the tissue grasping forceps with bowed out arcuate wide jaws attached first and second 90 degree angled extensions of the first and second arms.

In FIG. 8, the tissue forceps with a wide jaw design includes a non-arcuate terminal jaw of 2 cm that is perpendicular to the first and second arms of the tissue forceps. In this embodiment, there is no angled extension of the first and second arms at a 30 degree orientation to the longitudinal axis of the first and second arms. FIG. 9 discloses the embodiment of FIG. 3 but with a bowed-out configuration of the 2 cm long arcuate first and second jaws. FIG. 10 is an embodiment of the tissue forceps with bowed out arcuate wide jaws of 2 cm in dimension where the angled extension of the first and second arms of the tissue forceps are at a right angle of 90 degrees.

Figure 11:
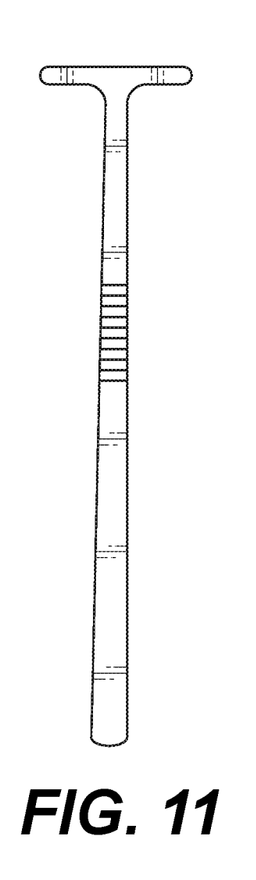
FIG. 11 is a top down view of the view of the tissue grasping forceps with wide jaws where there is no angled extension of the arm and where the first and second jaws are perpendicular segments smaller in dimension than those of FIG. 8 such that the distal portion of the arms are attached at their midpoints.
Figure 12:
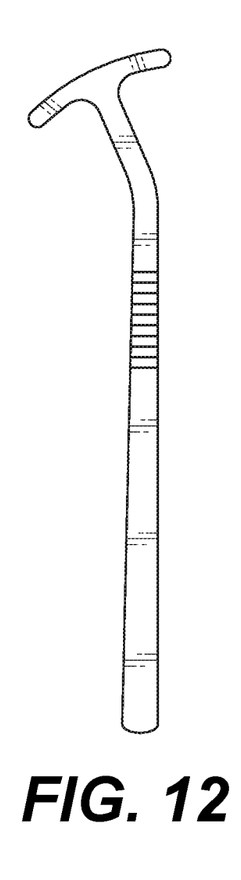
FIG. 12 is a top view of the tissue grasping forceps with bowed out arcuate wide jaws are smaller in dimension than those of FIG. 9 and attached first and second 30 degree angled extensions of the first and second arms.
Figure 13:
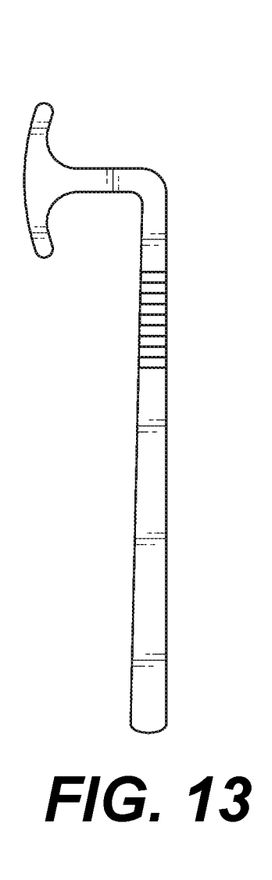
FIG. 13 is a top view of the tissue grasping forceps with bowed out arcuate wide jaws smaller in dimension than those of FIG. 10 and attached first and second 90 degree angled extensions of the first and second arms.

In FIG. 11, the tissue forceps with a wide jaw design includes a non-arcuate terminal jaw that is smaller than 2 cm and is perpendicular to the first and second arms of the tissue forceps. In this embodiment there is no angled extension of the first and second arms at a 30 degree orientation to the longitudinal axis of the first and second arms. FIG. 12 discloses the embodiment of FIG. 9 but with a bowed out configuration of a smaller than 2 cm long arcuate first and second jaws. FIG. 13 is an embodiment of the tissue forceps with bowed out arcuate wide jaws smaller than 2 cm in length where the angled extension of the first and second arms of the tissue forceps are at a right angle of 90 degrees.

The method involves the use of the device at an area of newly dissected tissue within a surgical operating field of a patient including the steps of: positioning the distal end of the tissue forceps such that the wide arcuate jaws are adjacent the newly dissected tissue; squeezing a first arm by applying pressure to a textured area along an outer surface of said first and to a corresponding outer surface of a second arm such that the arcuate jaws of the first arm and the second arm clamp down and engage each other sandwiching the dissected tissue at non-textured areas of a closing inner surface of the first and second jaws such that a plurality of serrated areas on said first and second jaws engage to shut the jaws and compress the dissected tissue to prevent bleeding from said dissected tissue.

It is to be understood that the method and device for grasping tissue using the tissue forceps with wide jaws is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A tissue forceps with wide jaws for compressing newly dissected tissue, comprising:
    a first arm traversing a first arm length, said first arm having a textured area on an outer surface of said first arm;
    a second arm traversing a second arm length where said second arm length is equal to said first arm length, wherein the first arm and the second arm form a vertex at a first proximal end of the first arm and second arm;
    a first extension extending from a distal end of said first arm away at a first extension angle with respect to a longitudinal axis of said first arm, wherein a distal end of said first extension terminates in a first forceps jaw; and
    a second extension extending from a distal end of said second arm away at a second extension angle with respect to a longitudinal axis of said second arm, wherein a distal end of said second extension terminates in a second forceps jaw, wherein said first forceps jaw has a first jaw length and said second forceps jaw has a second jaw length, wherein a first portion of an inner surface of said first forceps jaw has a plurality of first serrated surface areas, wherein a second portion of said inner surface of said first forceps jaw has a non-serrated surface area between a first serrated surface area of the plurality of first serrated surface areas and a second serrated surface area of the plurality of first serrated surface areas, wherein a first portion of an inner surface of said second forceps jaw has a plurality of second serrated surface areas, wherein a second portion of said inner surface of said second forceps jaw has a non-serrated surface area between a first serrated surface area of the plurality of second serrated surface areas and a second serrated surface area of the plurality of second serrated surface areas, wherein said first extension angle and said second extension angle are equal,
    wherein said first extension angle and said second extension angle are each 30 degrees, and
    wherein said first forceps jaw and said second forceps jaw are 2 cm in length and arcuate in shape.

2. The tissue forceps with wide jaws for compressing newly dissected tissue as recited in claim 1, wherein said first arm length and said second arm length are 12 cm.

3. The tissue forceps with wide jaws for compressing newly dissected tissue as recited in claim 1, wherein when said first arm and said second arm are configured such that when they are squeezed together by applying pressure at said textured area on said outer surface of said first arm and applying pressure at a corresponding outer surface on said second arm, the first forceps jaw and the second forceps jaw close together compressing said newly dissected tissue and preventing bleeding from said newly dissected tissue.

4. The tissue forceps with wide jaws for compressing newly dissected tissue as recited in claim 1, wherein said first forceps jaw and said second forceps jaw are in a bowed out orientation.

5. A method of compressing newly dissected tissue using tissue forceps with wide jaws as recited in claim 1, the method comprising:
 positioning the tissue forceps proximal to the newly dissected tissue such that the first arcuate forceps jaw and the second arcuate forceps jaw of the tissue forceps are adjacent the newly dissected tissue;
 squeezing the first arm of the tissue forceps connected to the first arcuate forceps jaw by applying pressure to a textured area along an outer surface of said first arm;
 squeezing the second arm of the tissue forceps connected to the second arcuate forceps jaw by applying pressure to a corresponding outer surface of said second arm of the tissue forceps such that the first arcuate forceps jaw and the second arcuate forceps jaw of the first arm and the second arm, respectively, clamp down and engage each other; and
 sandwiching the newly dissected tissue at non-textured areas of closing inner surfaces of the first arcuate forceps jaw and the second arcuate forceps jaw, respectively, such that a plurality of serrated areas on said first arcuate forceps jaw and said second arcuate forceps jaw engage each other and compress the newly dissected tissue to prevent bleeding from said newly dissected tissue.

\* \* \* \* \*